United States Patent [19]

Berger

[11] 4,105,465

[45] Aug. 8, 1978

[54] TREATED HYDRATED ALUMINA

[75] Inventor: Sidney Ethan Berger, Rye, N.Y.

[73] Assignee: Union Carbide Corporation, New York, N.Y.

[21] Appl. No.: 832,391

[22] Filed: Sep. 12, 1977

Related U.S. Application Data

[63] Continuation-in-part of Ser. No. 727,670, Sep. 29, 1976, abandoned.

[51] Int. Cl.$^2$ ................................................ C09C 1/40
[52] U.S. Cl. ........................... 106/308 Q; 106/288 B; 106/288 Q
[58] Field of Search ........... 106/288 B, 288 Q, 308 Q; 260/448.2 B

[56] References Cited

U.S. PATENT DOCUMENTS

| | | | |
|---|---|---|---|
| 3,227,675 | 1/1966 | Papalos | 106/308 Q |
| 3,350,345 | 10/1967 | Vanderbilt et al. | 106/308 Q |
| 3,839,065 | 10/1974 | Overhults et al. | 106/308 Q |

*Primary Examiner*—Winston A. Douglas
*Assistant Examiner*—J. V. Howard
*Attorney, Agent, or Firm*—Stanley Ktorides

[57] ABSTRACT

This invention is concerned with hydrated alumina, that is, aluminum trihydrate, coated with a silane containing three hydrolyzable groups bonded to a silicon atom thereof and containing at least one monovalent group which contains a polyalkylene oxide moiety therein, and/or hydrolyzates of such silanes and/or condensates of such hydrolyzates. Such treated hydrated alumina are useful in reinforced plastic compositions and in coatings.

6 Claims, No Drawings

TREATED HYDRATED ALUMINA

This application is a continuation-in-part of applicant's copending U.S. application Ser. No. 727,670, filed Sept. 29, 1976, now abandoned.

This invention is concerned with treated hydrated alumina, that is, alumina trihydrate, which contains on the surface thereof a specific silane composition which contains a silane possessing at least two to about three hydrolyzable groups bonded to the silicon thereof and an organic group which contains a polyalkylene oxide group. In the preferred composition of this invention, the polyalkylene oxide moiety is bonded to the silicon atom through an organic radical which is bonded to the silicon atom by a carbon to silicon bond.

THE PRIOR ART

Organosilicon compounds have for some time been employed in the treatment of inorganic oxide surfaces such as inorganic oxide films, particulate fillers and pigments, and fibers (such as glass fibers, aluminum fibers and steel fibers). Aluminum and steel fibers are regarded to be oxide surfaces because they are oxidized even though their sub-surfaces are not. The typical organosilicon treatment involves coating such surfaces with a hydrolyzate (and/or condensate of the hydrolyzate) of an organofunctional hydrolyzable silane. Such organofunctional hydrolyzable silanes are termed "Coupling Agent" and/or "Adhesion Promoter". The organofunctional groups typically contain groups reactive with complimentarily reactive groups in the medium in which the Coupling Agent is provided. The Coupling Agent is typically supplied to the surface of the inorganic oxide whereby through the hydrolyzable groups or silanol groups ($\equiv$Si—OH), bonding through siloxy moieties ($\equiv$Si—O—) is effected. Typical hydrolyzable groups include alkoxy of 1 to about 4 carbon atoms, alkoxyalkoxy containing up to about 6 carbon atoms, halogen such as chlorine, fluorine, and bromine, acyloxy of 2 to about 4 carbon atoms, phenoxy, and oxime. The preferred hydrolyzable groups are alkoxy, alkoxyalkoxy and acylocy. Common organofunctional groups are bonded to silicon by a carbon to silicon bond. The typical commercial functional radicals present in the organofunctional groups are vinyl, methacryloxy, primary amino, beta-aminoethylamino, glycidyl, epoxycyclohexyl, mercapto, polysulfide, ureido, and polyazamide. Another conventional technique for supplying the Coupling Agent to the inorganic oxide surface is by the integral blending technique. This technique involves adding to the resin medium the desired amount of the Coupling Agent and providing the medium in contact with the inorganic oxide surface by supplying the latter as a particulate filler or fiber to the medium or supplying the medium with the Coupling Agent to a continuous surface in the form of a film, fabric, foil or other shapes, wherein the Coupling Agent migrates within the medium to contact the surface or surfaces, react thereat and couple with the medium under the molding, curing and other shaping conditions.

As a rule, Coupling Agents enhance the chemical bonding between the medium and the inorganic oxide substrate whereby to achieve improved adhesion between them. This could affect the strength properties of the composite of the plastic or resin associated with the inorganic oxide substrate or substrates.

Apart from use of organofunctional silanes as Coupling Agents, they have been used, in selected cases, as fiber and fabric sizing agents and as pigment modifiers to alter dispersion characteristics in a given medium. Illustrative of these utilities, polyazamide silanes as disclosed in U.S. Pat. No. 3,746,748, patented July 17, 1973, are effective sizes for glass fiber woven fabrics, and methylsilanes have been employed to modify the dispersion characteristics of silica aerogels in silicone rubbers minimizing creep hardening of the silicone gum undergoing cure. The methyl groups in this case may be functional because the cure mechanism may attack them.

Silane Coupling Agents have been extensively employed in the surface treatment of inorganic particulate materials such as fillers, pigments, and materials which also act to reinforce the resin or plastic material in which it is incorporated such as asbestos fibers and relatively short length glass fibers, such as staple glass fibers. This important commercial area is termed glass fiber reinforced plastics ("GRP"). All of these have been beneficially treated by certain organofunctional silane Coupling Agents. However, in only rare instances do these Coupling Agents provide benefits other than increased adhesion. One particular exception is the use of vinyl silanes on aluminum trihydrate to enhance, to a limited degree, their dispersion in polyester resin systems.

Alumina trihydrate occurs naturally as the mineral gibbsite or hydrargyllite, or it is obtained directly from bauxite by the Bayer process which involves a treatment of bauxite with alkali under pressure. For some time it has been used as a flame retardant owing to its release, upon heating, of three molecules of water. This water makes up 35% of the weight of alumina trihydrate. This water loss begins at 250° C. and peaks sharply just above 300° C. (see J. F. Brown et al., J. Chem. Soc., 1953, pp. 84–88). A further characteristic of alumina trihydrate is that when it is used in large quantities in a resin system, as a filler, it provides low smoke levels when combustion occurs. Although alumina trihydrate is a relatively low cost fire retardant, on a common unit basis, large amounts of it are required to make a self-extinguishing (SE) product. In view of its adverse viscosity increases, as noted below, in GRP systems, and the further disadvantage that such large amounts of alumina trihydrate result in deleteriously affecting the physical properties of GRP composites, alumina trihydrate is seldom used alone in a GRP system to bring about the desired flame retardancy. As a rule, when using alumina trihydrate the art has also looked to the use of unsaturated chlorinated or brominated polyesters, antimony trioxide and/or the phosphorus compounds in combination to achieve the desired flame retardancy.

This invention recognizes that efforts to obtain favorable flame retardancy in glass fiber reinforced plastics ("GRP") based essentially on a conventional polyester and alumina trihydrate indicate critical problems in handling the loaded resin paste formed from the resin, the fiber content and the alumina trihydrate. The viscosity build-up derived from the inclusion of alumina trihydrate complicates the ability to achieve a system containing enough of the hydrate to give meaningful flame retardancy. The problem of filler loadings in GRP's is mentioned by W. S. Penn, "GRP Technology", Maclaren & Sons, Ltd., London, 1966, at pages 141–145.

A more detailed discussion of the prior use of aluminum trihydrate can be found in copending U.S. Application Ser. No. 727,936, filed on even date herewith.

DISCUSSION OF THE INVENTION

The novel treated aluminum trihydrate compositions of this invention find remarkable utility in plastic compositions insofar as they serve the function as a unique viscosity reducer when employed in combination with other filler or reinforcing materials typically employed in such plastic compositions. Thus the treated aluminum trihydrate of this invention when introduced into a plastic composition in combination with another filler, pigment and/or fibrous material will, in the typical case, greatly reduce the viscosity of the composition thereby allowing further amounts of the other filler, pigment and/or fibrous material to be added to the plastic composition, or more of the treated aluminum hydrate. The treated aluminum trihydrate of this invention also serves a function typical of aluminum trihydrate, that is, it serves to reduce the flammability properties of the plastic composition, in that it serves to help reduce the ability of the plastic composition containing the same from burning or supporting combustion. Moreover, the treated aluminum trihydrate of this invention can also contain other silane co-additives which co-react with the specific silane composition to enhance the ability of the aluminum trihydrate to reinforce the plastic matrix to which it is provided.

The specific organosilanes of this invention are characterized as structures having the following general formula:

$$R^{II}-(OR^I)_a ORSiX_3 \quad (I)$$

R in Formula (I) can be any divalent organic group which is either oxygen or carbon bonded to the silicon atom.

R may be any divalent radical which effectively joins the remainder of the molecule to the silicon atom. In essence, R is an inert moiety to the invention because the invention serves the function which contemplates two components joined together into one molecule. The first component is a hydrolyzable group characterized by the moiety — $SiX_3$ and the second component is the group characterized by the moiety -$(OR^I)_a$. Though typically the relationship of the two moieties to each other in the classical sense of Coupling Agents, assuming the -$(OR^I)_a$ moiety was termed organofunctional, would be dependent upon the size and chemical characterization of "R", that relationship is not apparent in the case of the instant invention. Thus given a particular "R", there exists an -$(OR^I)_a$ and $a = SiX_3$ combination which provides the advantages of this invention.

Usually, when R is an extremely large or bulky moiety, its impact upon the utility of the organosilane of formula (I) can be mitigated by increasing the size of $a$ and/or using a solvent, such as ethanol, when the silane supplied to the alumina trihydrate.

Though other desirable R's will be illustrated hereinafter, the preferred R is an alkylene group containing from 1 to about 8 carbon atoms, preferably 2 to about 6 carbon atoms. $R^I$ is one or more 1,2-alkylene groups each containing at least 2 carbon atoms and typically not more than about 4 carbon atoms, preferably $R^I$ is ethylene. $R^{II}$ is hydrogen, an alkyl group containing 1 to about 8 carbon atoms, preferably 1 to about 4 carbon atoms, acyloxy (of 2 to about 4 carbon atoms) or an organofunctional group as defined below for $R^3$, X is a hydrolyzable group such as alkoxy containing, for example, 1 to about 4 carbon atoms, alkoxyalkoxy in which the terminal alkyl contains 1 to about 4 carbon atoms and the internal alkyl is alkylene which contains 2 to about 4 carbon atoms and is preferably ethylene; acyloxy such as acetoxy, propionoxy and the like; aryloxy such as phenoxy, para-methylphenoxy, oximes, and the like. In formula (I), $a$ is a number having an average value of 4 to about 150, preferably about 4 to about 120.

the silane of formula (I) in a preferred embodiment is described in U.S. Pat. No. 2,846,458, patented Aug. 5, 1958. A particular illustration of that silane is set forth at Column 3, line 20 et sequence of the aforestated patent. However, this invention is not to be construed as limited to the particular silanes which are described in the patent. For example, the patent is exceedingly restrictive in terms of the description of the divalent organic group which joins the polyether to the silicon atom. In accordance with this invention, that divalent organic group encompasses a much greater class of moieties.

Illustrative of the expanse of moieties encompassed by R above, are the following:

—$CH_2CH_2CH_2$—;

—$CH_2CH_2$—;

—$CHCH_2$—;
   |
   $CH_3$

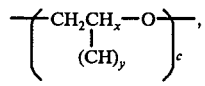

wherein c is 1 to about 20, x is 1 when y is 1, and 2 when y is 0, and y is 0 or 1;

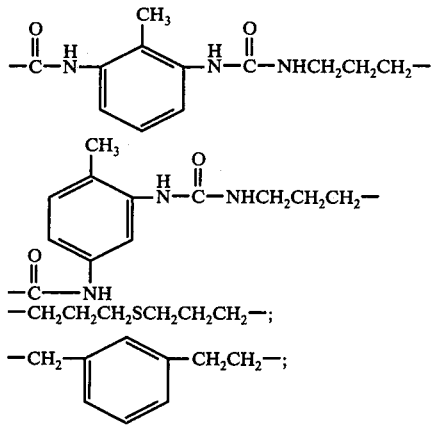

—$CH_2CH_2CH_2SCH_2CH_2CH_2$—;

and the like.

As can be seen from the above, the characterization of R is exceedingly diverse and its ultimate limits have not been ascertained except insofar as all experimental evidence has indicated that it constitutes a basically inert component as compared to the function of the hydrolyzable silicon moiety and the separate polyether moiety as characterized above.

Illustrative of the -$(OR^I)_a$ positive of the silanes of formula (I) is the following:

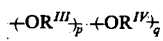

in which $R^{III}$ and $R^{II}$ are different 1,2-alkylene radicals, in which $R^{III}$ is ethylene and $R^{IV}$ is 1,2-propylene or 1,2-butylene, $p$ is a number greater than $q$ and the sum of $p$ and $q$ is equal to the value of $a$.

The silanes of formula (I) may be used alone or in combination with another and different silane, such as one encompassed by formula:

$$R^3_n(SiX_{4-n})_b \qquad (II)$$

or the cohydrolyzate or the cocondensate of such silane with that of Formula (I) above. In formula (II), $n$ is equal to 0 or 1 and $R^3$ is an organic radical whose free valence is equal to the value of $b$ and can be an alkyl group of 1 to about 18 carbon atoms, preferably about 3 to about 14 carbon atoms, or an organofunctional group bonded to silicon by a carbon to silicon bond. The organofunctional group thereof may be one or more of the following illustrative groups; vinyl, methacryloxymethyl, gamma-methacryloxypropyl, aminomethyl, beta-aminopropyl, gamma-aminopropyl, delta-aminobutyl, beta-mercaptoethyl, gamma-mercaptopropyl, gamma-glycidoxypropyl, beta-(3,4-epoxycyclohexyl)ethyl, gamma-chloro-isobutyl, polyazamides such as described in U.S. Pat. No. 3,746,348, gamma-(beta-aminoethyl)-aminopropyl, (ethylene beta-aminoethyl) methacryl ammonium hydrohalide, beta-(4-vinylbenzyl) (ethylene-beta-aminoethyl) ammonium hydrohalide, and the like. Any organo functional hydrolyzable silane suitable for use as a Coupling Agent may be employed in combination with the silane of formula I. In formula (II), $b$ is a positive number, generally 1 and typically not greater than about 5.

When there is employed a combination of or coreaction products of the silanes of formulas I and II, the amount of silane of formula I employed should be that amount which provides a viscosity reduction and other advantages as herein defined. Any amount of the silane of formula II may be employed so long as such does not hinder the role of the silane of formula I.

The silane of formula (I) can be separately employed with the silane of formula (II). For example, they can both be applied neat or from aqueous solution to the substrate simultaneously or in sequence, or they can be premixed and supplied to the treated surface together as a mixture of co-reaction product. The maximum amount of reaction of the silanes is less than that amount of condensation from the hydrolysis products which renders the condensation product in an aqueous solution which may or may not contain a water soluble solvent such as ethanol.

Illustrative of the diversity of organosilanes covered by formula (I) are the following:

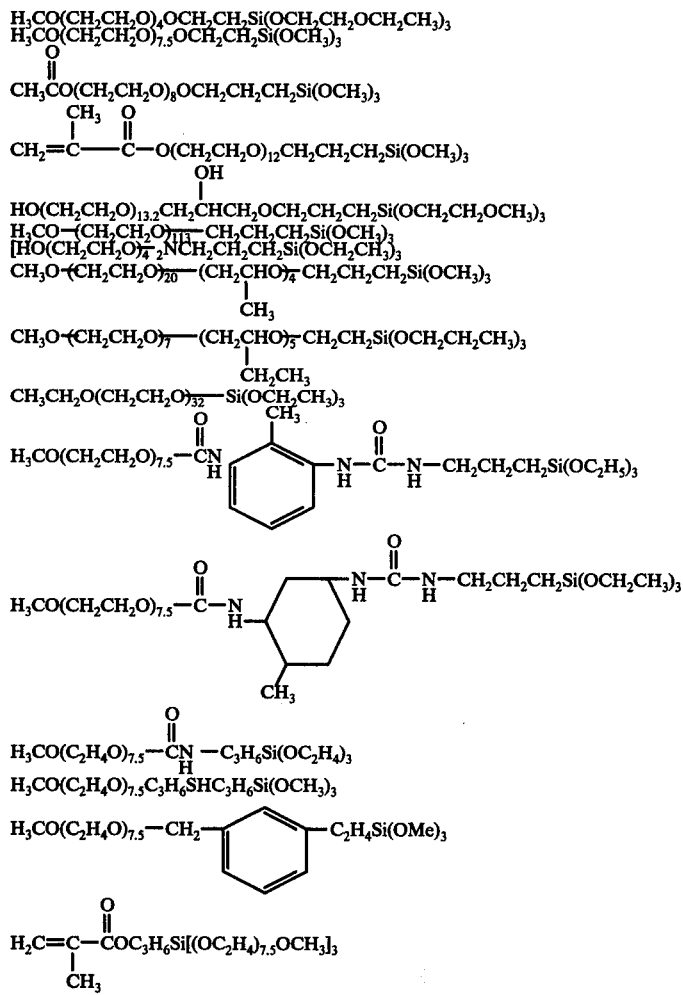

Suitable silanes of formula II useful in the practice of this invention include, by way of example only, the following:
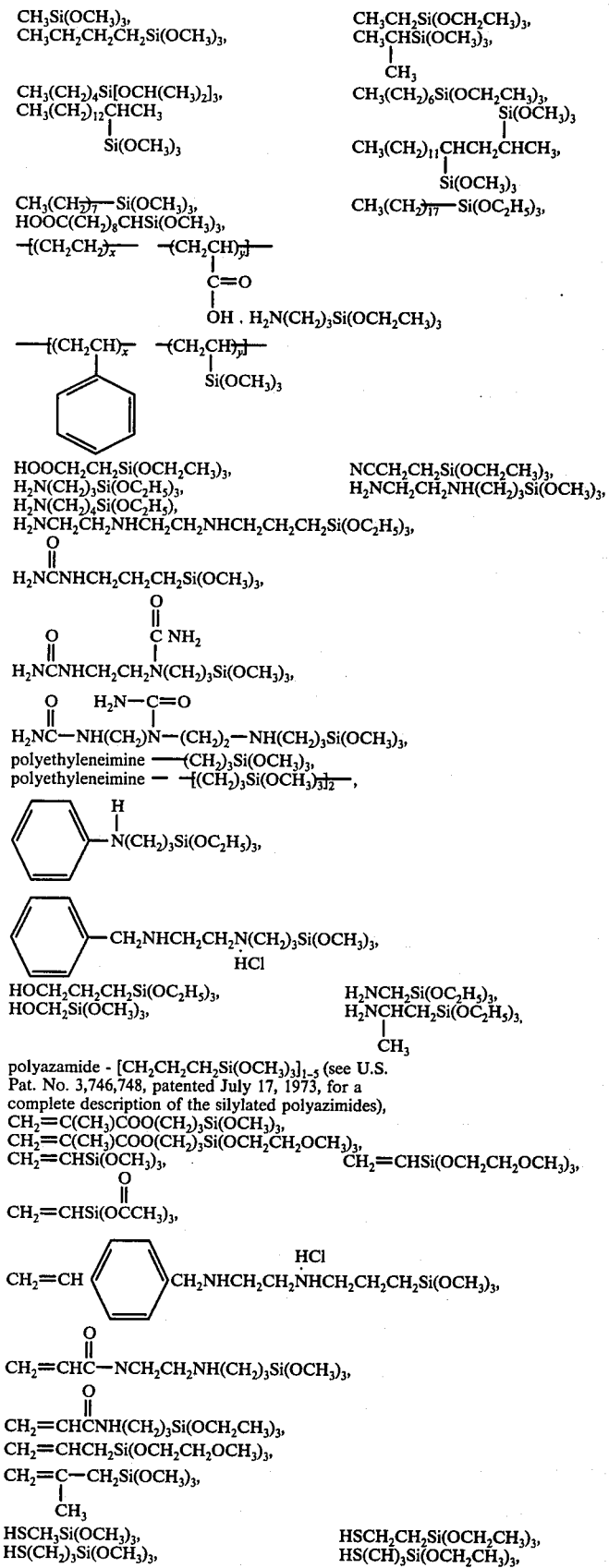

-continued

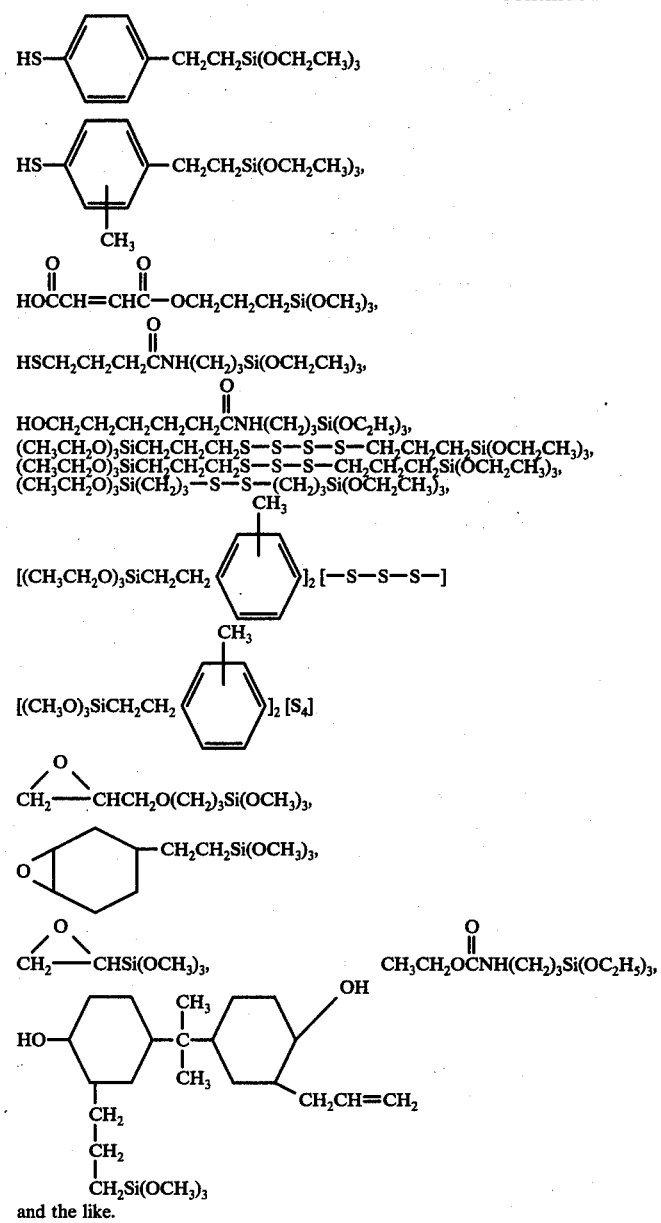
and the like.

Because the aforementioned silanes do not serve a function that is equivalent to the function of a Coupling Agent, it would be improper to characterize them as a member of that class of materials and hence their role in providing strength is not such a factor as to make the size of the particulate alumina trihydrate significant in the enjoyment of this invention. For that reason, the silanes of formula (I) are hereinafter to be termed a "Dispersion Promoter", that is, a material which makes the inorganic oxide or other particulate material more compatible or dispersible within the plastic or resin system in which it is supplied. In one sense the silanes used in this invention serve the function of a surface active agent and in another sense they possess the capacity of enhancing bonding between the inorganic oxide and the resin or plastic in which it is provided. Such bonding is effected by virtue of interface compatibility, and/or by way of associative or hydrogen bonding or through covalent bonding to the extent (generally a minimal factor) that the silane possesses organo functional moieties of the classical kind found in Coupling Agents.

One feature of the Dispersion Promoters of this invention is that they alter the surface characteristics of the inorganic oxide so that they are more readily and more thoroughly dispersed within the resin or plastic in which they are incorporated and this serves to enhance the appearance of the resulting composite and increase the overall strength of the composite when the particulate material employed is one which serves to reinforce the plastic or resin. This invention is concerned with surface treated particulates where the surface treatment is either the addition of the aforementioned Dispersion Promoters or its hydrolyzate or partial condensate of the hydrolyzate (or the cohydrolyzates or cocondensates thereof) to the surface of the inorganic oxide.

The amount of Dispersion Promoter provided upon the alumina trihydrate, as characterized herein, is that amount which alters the surface characteristics of the particles so that they are more readily dispersed within the resin or plastic or other medium in which they are incorporated. Typically, the amount of the Dispersion Promoter [or its hydrolyzate or partial condensate of the hydrolyzate (or the cohydrolyzate or condensates thereof as characterized above in regard to the utilization of the silanes of Formula (II)) — hereinafter collectively termed "its derivatives"] which is supplied to the alumina trihydrate may be as little as 0.25 weight percent to as much as 5 weight percent, based upon the combined weight with the alumina trihydrate particles. As a rule, about 0.5 to about 3 weight percent of the Dispersion Promoter and/or its derivatives is adequate for the purposes of appropriately alternating the surface characteristic of the alumina trihydrate particles. However, greater concentrations may be used for purposes which exclude the simple utilization of the so treated alumina trihydrate particles in plastics or resins.

The Dispersion Promoter and/or its derivatives may be provided on the alumina trihydrate particles by any of the known methods by which Coupling Agents are similarly supplied to particulate surfaces. Thus spraying the Dispersion Promoter while tumbling the particles or mixing the particles in a dilute liquid composition containing the Dispersion Promoter and/or its derivative represent adequate treating procedures.

The plastics and/or resin in which the alumina trihydrate particles treated with the Dispersion Promoter and/or its derivatives include essentially any plastic and/or resin. Included in the definition of plastic are rubber compounds. The treated alumina trihydrate particles may be supplied to the plastic and/or resin while the same is in any liquid or compoundable form such as a solution, suspension, latex, dispersion, and the like. It makes no difference from the standpoint of this invention whether the plastic contains solvent or nonsolvent, or the solvent is organic or inorganic except, of course, it would not be desirable for any plastic or resin or any of the treated alumina trihydrate to employ a solvating or dispersing medium which deleteriously affects the components being blended.

Suitable plastics and resins include, by way of example, thermoplastic and thermosetting resins and rubber compounds (including thermoplastic elastomers). The plastics and resins containing the treated particles of this invention may be employed, for example, for molding (including extrusion, injection, calendering, casting, compression, lamination, and/or transfer molding), coating (including laquers, film bonding coatings and painting), inks, dyes, tints, impregnations, adhesives, caulks, sealants, rubber goods, and cellular products. Thus the choice and use of the plastics and resins with the treated particles of this invention is essentially limitless. For simple illustration purposes, the plastics and resins may be alkyd resins, oil modified alkyd resins, unsaturated polyesters as employed in GRP applications, natural oils, (e.g., linseed, tung, soybean), epoxides, nylons, thermoplastic polyester (e.g., polyethyleneterephthalate, polybutyleneterephthalate), polycarbonates, polyethylenes, polybutylenes, polystryenes, sytrene butadiene copolymers, polypropylenes, ethylene propylene co- and terpolymers, silicone resins and rubbers, SBR rubbers, nitrile rubbers, natural rubbers, acrylics (homopolymer and copolymers of acrylic acid, acrylates, methacrylates, acrylamides, their salts, hydrohalides, etc.), phenolic resins, polyoxymethylene (homopolymers and copolymers), polyurethanes, polysulfones, polysulfide rubbers, nitrocelluloses, vinyl butyrates, vinyls (vinyl chloride and/or vinyl acetate containing polymers), ethyl cellulose, the cellulose acetates and butyrates, viscose rayon, shellac, waxes, ethylene copolymers (e.g., ethylene-vinyl acetate copolymers, ethylene-acrylic acid copolymers, ethylene-acrylate copolymers), and the like.

The alumina trihydrate particles treated with the Dispersion Promoter has greater affinity for water and as a consequence they are more readily dispersible in water containing systems. The treated particles are more readily incorporated in and stay dispersed longer and more uniformly in water containing systems such as latexes, water solutions, and water dispersions regardless of whether water is the continuous or discontinuous phase. In addition the Dispersion Promoter enhances the dispersibility of the treated alumina trihydrate in organic solvents ranging from hydrocarbon liquids to highly polar organic liquids.

Though this invention has been described in great detail, the following examples are provided to demonstrate specific illustrations of the invention.

EXAMPLE 1

1135 grams of a precipitated alumina trihydrate, Al(OH)$_3$, of 1.0 micron particle size, such as Hydral TM 710 manufactured by the Aluminum Company of America, were charged to an 8 quart Patterson Kelly TM twin shell blender. With the shell rotating and the intensifier bar operating, 393.3 grams of each silane listed in Table 1 below were fed through the liquid entry port over a period of 15 minutes. The silane charge corresponded to about 25 percent by weight on the completed silane concentrate. An extra 15 grams of silane was included in the charge to compensate for liquid hold-up in the system. After all the silane was added, blending was continued for an additional 15 minutes with the intensifier bar operating.

TABLE 1

| Silane | Composition |
|---|---|
| A | $H_3CO(C_2H_4O)_{7.5}C_3H_6Si(OCH_3)_3$ |
| B | $H_3CO(C_2H_4O)_{113}C_3H_6Si(OCH_3)_3$ |
| C | $H_3CO(C_2H_4O)_{7.5}C(O)NH$-(CH$_3$-phenyl)-NHC(O)NHC$_3$H$_6$Si(OC$_2$H$_5$)$_3$ |
| D | $H_3CO(C_2H_4O)_{7.5}C(O)NH-C_3H_6Si(OC_2H_5)_3$ |
| E | $H_3CO(C_2H_4O)_{7.5}C_3H_6SC_3H_6Si(OCH_3)_3$ |
| F | $H_3CO(C_2H_4O)_{7.5}CH_2$-phenyl-$C_2H_4Si(OMe)_3$ |
| G | $H_2C=C(CH_3)-C(O)OC_3H_6Si[OC_2H_4)_{7.5}OCH_3]_3$ |

SILANE A Preparation of $CH_3O(C_2H_4O)_{7.5}C_3H_6Si(OCH_3)_3$

Into a 1 liter 3 necked flask equipped with electric heating mantle, mechanical stirrer, thermometer, liquid dropping funnel and water cooled condenser is charged 398 gms., 1.0 mole, of $CH_3O(C_2H_4O)_{7.5}CH_2CH=CH_2$, prepared by reaction of CARBOWAX® Methoxy Polyethylene Glycol 350 (Made by Union Carbide Corporation, New York, N.Y., U.S.A.) with stoichiometric sodium methoxide and allyl chloride in toluene solution, and 30 parts per million (ppm) of platinum added as a 5% solution of $H_2PtCl_6 \cdot nH_2O$ (40% Pt) in isopropanol. By means of the dropping funnel, 149.0 gms., 1.1 moles, of $HSiCl_3$ is slowly added over a period of 1 hour beginning at 30° C. Heating is continued from 50 to 60° C for 1 hour to complete reaction and excess unreacted $HSiCl_3$ is recovered by distillation to a final pot temperature of 100° C. There results about 533 gms., 1.0 moles, of $CH_3O(C_2H_4O)_{7.5}C_3H_6SiCl_3$ in near quantitative yeild, which analyzes 5.5 meg./gm of silyl chloride acidity as measured by titration with a 0.1 N solution of sodium hydroxide. The latter chlorosilane adduct is treated over a period of 2 hours with excess methanol while heating at 70°–80° C and maintaining continuous evacuation of by-product hydrogen chloride by means of a water aspirator. There results 520 gms., 1.0 mole, of $CH_3O(C_2H_4O)_{7.5}C_3H_6Si(OCH_3)_3$ in quantitative yield, containing less than 0.1 meg/gm. titratable acidity. SILANE B Preparation of $CH_3O(C_2H_4O)_{113}C_3H_6Si(OCH_3)_3$ Starting with 250 gms., 0.05 moles of toluene diluted CARBOWAX Methoxy Polyethylene Glycol 5000 in a 1 liter, 3-necked flask equipped with thermometer, mechanical stirrer, electrical heating mantle and distillation head, successive treatment in the conventional manner with .065 moles of sodium methoxide and 5 gms., 0.65 moles of allyl chloride produces a 50 wt % toluene solution of the corresponding allyl ether capped derivative $CH_3O(C_2H_4O)_{113}CH_2CH=CH_2$. Subsequent reaction of 447 gms. of the latter with 5.4 gms., 0.0438 moles, of $HSi(OCH_3)_3$ in the presence of 0.057 gms. of $H_2PtCl_6$, diluted to 1.09 ml in isopropanol and 0.4 gms. of glacial acetic acid is continued at about 55° C for two hours until complete. Toluene and other volatiles are removed by vacuum stripping to a final temperature of 60° C. The resulting product $CH_3O(C_2H_4O)_{113}C_3H_6Si(OCH_3)_3$ is diluted to 40 wt % solids in toluene.

SILANE C Preparation of

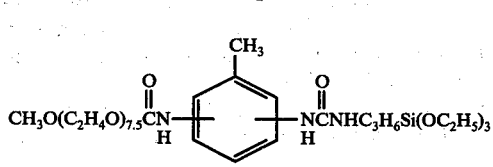

Into a 1 liter, 3-necked flask equipped with thermometer, mechanical stirrer, electric heating mantle and distillation head is charged 150 gms. toluene and 262.5 gms., 0.75 moles, of UCC CARBOWAX Methoxy Polyethylene Glycol 350. Distillation of 40 gms. of toluene is used to remove traces of contained moisture and thereupon is added 130.6 gms., 0.75 moles, of 80/20 isomeric mixture of 2,4 and 2, 6-toluene diisocyanate over a period of 1 hour beginning at about 0° C. Stirring is continued for 1 hour as the reaction mixture slowly exotherms to about 15° C and is finally warmed to about 28° C. By means of a liquid addition funnel is added 165.9 gms., 0.75 moles, of $NH_2(CH_2)_3Si(OC_2H_5)_3$, and external cooling is provided to maintain a maximum reaction temperature of 25° C. Additional toluene, 100 ml., is added to dissolve resulting solids that form. After stirring 1 hour to complete reaction toluene is removed by vacuum stripping to a final condition of about 1 mm. of mercury pressure at 50° C and the resulting 559 gms., 0.75 moles of

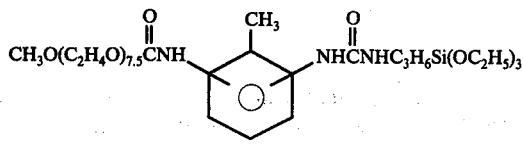

is observed as a waxy solid and is diluted with 50 wt % of anhydrous absolute ethanol.

SILANE D Preparation of

Into a 1 liter, 3-necked flask equipped as previously described for silane C is charged 297.5 gms., 0.85 moles of CARBOWAX Methoxy Polyethylene Glycol 350 and 130 gms. of toluene. After heating to 120° C and distilling 40 gms. of toluene to insure removal of trace moisture, 210 gms., 0.85 moles of $O=C=N(CH_2)_3Si(OC_2H_5)_3$ containing 1 gm. of dissolved dibutyl tin dilaurate is slowly added over 1 hour beginning at 0° C and finally reaching 25° C. Vacuum stripping to 1 mm. mercury pressure at 80° C provides 507 gms. of

which is subsequently diluted to 75 wt % solids in anhydrous absolute ethanol.

SILANE E Preparation of $CH_3O(C_2H_4O)_{7.5}C_3H_6SC_3H_6Si(OC_2H_5)_3$

Into a 1 liter, 3-necked flask equipped as previously described in Example C is charged 380 gms., 0.95 moles, of allyl ether of CARBOWAX Methoxy Polyethylene Glycol 350, 186.4 gms., 0.95 moles, of $HS(CH_2)_3Si(OCH_3)_3$ and 2.3 gms. of N,N-bis-azoisobutyronitrile. Upon heating the stirred mixture to about 85° C, an exothermic heat rise to 120° C is observed and maintained for about 1 hour. Upon cooling to 25° C there results 566 gms., 0.95 moles of $CH_3O(C_2H_4O)_{7.5}C_3H_6SC_3H_6Si(OCH_3)_3$ which is diluted to 80 wt % solids with anhydrous absolute ethanol.

SILANE F Preparation of

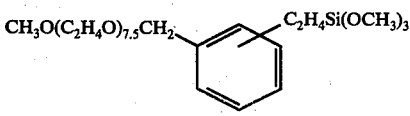

Starting with 315 gms., 0.9 moles of CARBOWAX Methoxy Polyethylene Glycol 350 and 100 ml. of toluene in much the same equipment set up as previously described for silane B, reaction with 0.9 moles of sodium methoxide by removing methanol provides the sodium salt derivative, $CH_3O(C_2H_4O)_{7.4}Na$. Slow addition of 247.4 gms., 0.9 moles, of

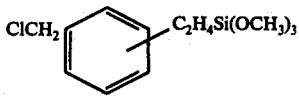

over 1 hour produces an exothermic heat rise from 50° to 90° C and an increasing amount of finely dispersed NaCl. When reaction is complete, cool to 25° C., filter free of salt, remove toluene under vacuum to obtain 527 gms. of

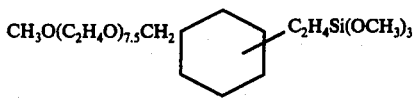

which is diluted to 80 wt % solids with anhydrous absolute ethanol.

SILANE G Preparation of

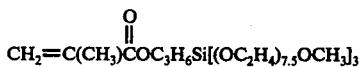

Into a liter, 3-nicked flask equipped with thermometer, mechanical stirrer, electric heating mantle distillation head and receiver assembly is charged 333 gms., 0.95 moles of CARBOWAX Methoxy Polyethylene Glycol 350, 236 gms., 0.95 moles of

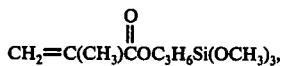

5.7 gms. of tetra-isopropyl titanate and 0.22 gms. of monomethyl ether of hydroquinone. Heat is applied to maintain a (maximum) reaction temperature of 100° C over a period of 6 hours while retaining 19 gms. of methanol as distillate. Most of the remainder of [30.4 gms. theoretical] methanol is removed by vacuum stripping at 25° to 50° C to a final condition below 1 mm. of mercury pressure. There results 538.6 gms. of

which is diluted with anhydrous absolute ethanol to 80 wt % solids.

EXAMPLE 2

Separate quantities of 3456 grams of alumina trihydrate of 6 to 9 micron particle size, such as Alcoa C-331 or Great Lakes Foundry Sand GHA-331, were combined with 144 grams of each of the dry silane concentrates described in Example 1 above. The mixtures were each blended for two hours in the twin shell blender and stored for subsequent testing. The average silane concentration in each of the mixtures was 1.0 weight percent.

For comparative purposes, 5, 15 and 25 percent of the 1 micron alumina trihydrate (Hydral 710) without any silane was blended with the 6 to 9 micron alumina trihydrate (GHA-331).

EXAMPLE 3

Separate quantities of 200 grams of Marco ™ GR 13021 Polyester Resin* (Sold by W. R. Grace & Co.) were weighed into a one pint tin lined can. 350 grams (175 phr) each of the alumina trihydrate fillers, as characterized in Table 2 below, were slowly added to the resin with gentle hand stirring to promote wetting of the filler by the resin. When all of the filler had been added, the can was covered and mixed with an electrically powered Jiffy ™ Mixer Blade (Model LM, Jiffy Mixer Co.) for 15 minutes.

*Based upon infrared and nuclear magnetic residence analysis, an idealized segmented chemical representation of this resin, deduced from calculated mole ratios of phthalate, fumarate, 1,3 butane diol and ethylene glycol (as ester groups) is

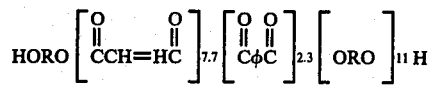

in which ORO diol units = 1.8/1.0 mole ratio of 1,3 butane diol/ethylene glycol. The resin contains styrene monomer.

The can of resin-filler mix was conditioned in a constant temperature water bath controlled at 90° F ± 1° F for two hours. Viscosity of the mix was then determined with a Brookfield ™ Synchro-Electric Viscometer ™ Model HBT, using spindle No. 4 which had also been similarly conditioned for two hours at 90° F.

TABLE 2

| Experiment No. | Filler Mixed with resin | Viscosity, 10 RPM $10^3$ cps |
|---|---|---|
| a. | Untreated alumina Trihydrate (GHA-331) | 78.4 |
| b. | 75 wt. % GHA-331/25 wt. % Hydral 710 from Example 2 | 60.0 |
| c. | 85 wt. % GHA-331/15 wt. % Hydral 710 from Example 2 | 44.0 |
| d. | 95 wt. % GHA-331/5 wt. % Hydral 710 from Example 2 | 56.0 |
| e. | 96 wt. % GHA-331/4 wt. % Hydral 710 containing 25% Silane A from Example 2 | 28.8 |

These data show the well known viscosity lowering effect of filler packing and that a minimum viscosity with untreated Hydral 710 is achieved at 15 percent in a blend with GHA-331.

But the presence of Silane A on the Hydral 710 carrier reduces viscosity by a factor of 2.

EXAMPLE 4

The alumina trihydrate fillers from Example 3 were compared in the following bulk molding compound (BMC) formulation:

| Component | Description | Parts by Weight | Grams |
|---|---|---|---|
| Marco™ GR 13021[1] | Unsaturated polyester resin in styrene monomer | 80. | 200. |
| BAKELITE™ LP-40A[2] | Low profile additive: an acrylic acid modified poly (vinyl acetate) in styrene monomer. | 20. | 50. |
| Zinc Stearate | Mold release agent | 2. | 7.5 |
| Tert butyl perbenzoate | Cross-linking catalyst | 1. | 2.5 |
| GHA-331[3] (See Table 3 below) | Al(OH)$_3$ 6.5–8.5 avg. particle size | 275. | 687.5 |
| Glass P-265A[4] × 1 | ¼" chopped glass | | |

| Component | Description | Parts by Weight | Grams |
|---|---|---|---|
| | strand | 76.3 | 190.7 |

(1) W. R. Grace & Co., Polyester Division - Marco
(2) Union Carbide Corporation
(3) Great Lakes Foundry Sand Co., Mineral Products Division
(4) Owens-Corning Fiberglas Corporation The procedure for compounding the formulation was as follows:

The resin, low profile, additive, zinc stearate, and t-butyl perbenzoate were preblended in a one pint wide mouth jar with an air driven "Lightnin" mixer and Jiffy® stirring blade which consisted of a horizontal two bladed propeller with guard ring, and two vertical blades. Care was taken to insure complete dispersion of the zinc stearate in the mutually soluble resin and low profile additive.

The liquid pre-blend was transferred to the (1 gallon) bowl of a Hobart ™ N-50 mixer equipped with a dough hook. The 687.5g of Al(OH)$_3$ was added in each instance in one charge with the mixer stopped. The mixer was then run at speed number one for exactly six minutes. During this period the time for the untreated and treated Al(OH)$_3$ fillers to be completely wetted by and dispersed in the liquid phase was recorded and set forth in Table 3.

TABLE 3

| Experiment No. | Alumina Trihydrate | Time for Wet Out and Dispersion in Liquid Phase, seconds |
|---|---|---|
| a. | Untreated GHA-331 | 180 |
| b. | 85 wt. % Untreated GHA-331/15 wt. % Hydral 710 from Example 2 | 160 |
| c. | 96 wt. % untreated GHA-331/4 wt. % Hydral 710 containing 25% Silane A from Example 2 | 60 |

With the mixer stopped, the filled resin was scraped from the sides of the bowl, down into the center, and the first increment of glass charge was added around the wall of the bowl to prevent resin from readhering. The mixer was then run at speed number one and the entire 190.7 gram glass charge added in exactly two minutes. Mixing was continued another two minutes for a total mixing time of four minutes. Commercial practice is to minimize mixing to avoid fiber degradation. The compound was then molded into test plaques.

Test plaques were prepared by charging 400 grams of the above compounds to a single cavity 8 × 8 × 0.125 inches, chrome plated mold. Top and bottom surfaces were lined with 0.003 inches thick MYLAR® film. Press cycle was two minutes at 300° F under 40 tons of force.

The resulting plaques were examined visually for uniformity of glass dispersion. The pronounced dark gray swirl pattern with untreated alumina trihydrate is glass. The lighter areas are resin-rich, resulting from incomplete dispersion of glass during mixing in the Hobart and/or "washing" of the resin from the glass as the compound flowed in the mold. Thus, the less the visual contrast in a plaque, the better the uniformity of glass dispersion.

A visual qualitative assessment of glass dispersion is set forth in Table 4 which is keyed to the experiment numbers of Table 3.

TABLE 4

| Experiment Nos. | Alumina Trihydrate | Dispersion Quality |
|---|---|---|
| a. | Untreated GHA-331 | Fair |
| b. | 85 wt. % untreated GHA-331/ 15 wt. % Hydral 710 from Example 2 | Fair |
| c. | 96 wt. % untreated GHA-331/ 4 wt. % Hydral 710 containing 25% Silane A from Example 2 | Good |

The molded plaques were sawed into 3 × 0.5 × 0.161 – 0.233 inches thick test specimens (depending on plaque thickness). Five specimens per plaque were selected randomly for flexure testing by ASTMD 790-71 and the results are shown below:

| Alumina Trihydrate | Flexural Strength, psi | Standard Error, % |
|---|---|---|
| Untreated GHA-331 | 8,070 | 27 |
| 96 wt. % untreated GHA-331/ 4 wt. % Hydral 710 containing 25% Silane A from Example 2 | 12,334 | 13 |

The reduced standard error is additional evidence of improved plaque uniformity with silane treated alumina trihydrate. The definition for "standard error" can be found in Rickmers et al., *Statistics, An Introduction*, page 22 (1967), published by McGraw-Hill Book Company, New York, N.Y.

EXAMPLE 5

Separate quantities of 1816 grams of GHA-331 were charged to an 8 quart Patterson Kelly Liquid-Solid ("twin-shell") Blender. With the blender and intensifier rotating, 150 ml of treating solution of compositions described below were gravity fed, via separatory funnel, to the inlet tube over a period of approximately 15 minutes. The blender and intensifier were allowed to run another 15 minutes to assure adequate liquid-solid dispersion and to minimize agglomerate formation.

The treated contents of the blender were spread to a one inch depth in a 14 × 18 inch tray and dried for one hour at 100° C.

Each treating solution was prepared by diluting 18.16 grams of one of the silanes described in Example 1 to 150 ml with a 10 volume % water - 90 volume % methanol solution which was mixed for about 10 minutes before feeding to the twin shell blender.

EXAMPLE 6

Resin-alumina trihydrate mixtures and viscosity measurements were made as in Example 3, except that a Brookfield Model RVT Viscometer with a No. 6 Spindle was used. The following viscosisty data with silane treated filler from Example 5 show the effectiveness of silylated polyethers in viscosity reduction. Comparison of Silane A performance with that of its polyether intermediate shows the contribution of the silane moiety.

| Alumina Trihydrate Filler Pretreatment (1 wt. %) | Resin-Filler Viscosity at 10 RPM, $10^3$ cps | |
|---|---|---|
| | Run #1 | Run #2 |
| None (Control) | 66.7 | 86.5 |
| Silane A $H_2C=CHCH_2O(C_2H_4O)_{7.5}CH_3$ | 17.8 | — |

-continued

| Alumina Trihydrate Filler | Resin-Filler Viscosity at 10 RPM, $10^3$ cps | |
|---|---|---|
| Pretreatment (1 wt. %) | Run #1 | Run #2 |
| (used to make A) | 50.5 | — |
| Silane B | 37 | 34.0 |
| Silane C | — | 64.5 |
| Silane D | — | 44.0 |
| Silane E | — | 36.5 |
| Silane F | — | 38.5 |
| Silane G | — | 53.0 |

EXAMPLE 7

The pretreated alumina trihydrate fillers of Example 5 were compounded into the bulk molding compounds of Example 4. The effectiveness of Silanes A–F and the effectiveness of Silane A over its polyether precursor are shown below.

| Silane on Alumina Trihydrate | Filler Wetout Time, sec. | Glass Dispersion Uniformity | Flexural Strength psi | Run No. |
|---|---|---|---|---|
| None | 240 | Poor | 7,570 | 1 |
| Silane A | 90 | Good | 10,450 | 1 |
| $H_2C=CHCH_2O(C_2H_4)_{7.5}CH_3$ | 120 | Fair | 8,625 | 1 |
| None | 165 | Poor | 8700 | 2 |
| Silane B | 75 | Good | 11,300 | 2 |
| Silane C | 140 | Poor | 10,800 | 2 |
| Silane D | 70 | Fair | 9,990 | 2 |
| Silane E | 70 | Fair | 10,000 | 2 |
| Silane F | 85 | Good | 8,100 | 2 |
| Silane G | 125 | Fair | 9,800 | 2 |

Silane C reduces wet out time and improves flexural strengths. In the case of Silane C the magnitude of wet out time reduction would be greater and glass dispersion would be better if the ethylene oxide chain length were increased to compensate for the hydrophobic effect of the tolyl urethane moiety.

EXAMPLE 8

The dry silane concentrate (DSC) consisted of 25.0 wt % the silane composition of one (1) mole of $H_2C=C(CH_3)COO(CH_2)_3Si(OCH_3)_3$ and two (2) moles of $(H_3CO)_3Si(CH_2)_3(OC_2H_4)_{7.5}OCH_3$, mole ratio of 1:2, on Hydral 710. This was accomplished by first "fluffing" the Hydral 710 in a twin shell blender which amounted to breaking up any clumps with the high speed intensifier bar and thereby increasing the surface area. The Hydral 710 was then transferred to a Hobart mixing bowl (1 gallon) were the appropriate amount (25 wt%) of the silane composition was applied neat by means of hand spraying and mixing. After complete application of the silane composition, the alumina trihydrate was returned to the twin shell blender to break up any clumps which might have formed. A blend was made by placing, in a twin shell blender, the appropriate amount of DLC and untreated GHA-331 which would equal 1.0 wt % of the silane composition based on total alumina trihydrate weight. The blender was then run for 10 minutes and the alumina trihydrate was removed.

EXAMPLE 9

The following formulation was employed to make a bulk molding compound (BMC):

| Component | Parts by Weight | Grams |
|---|---|---|
| Marco GR 13021 polyester[1] | 80 | 200 |
| Bakelite LP-40A[2] | 20 | 50 |
| Zinc Stearate | 3 | 7.5 |
| Tertiary butyl perbenzoate | 1 | 2.5 |
| GHA-331[3] | 275 | 687.5 |
| OCF P-265A × 1[4] ¼" chopped fiberglass strand | 76.3 | 190.7 |

[1]W.R. Grace & Co., Polyester Division - Marco
[2]Union Carbide Corporation
[3]Great Lakes Foundry Sand Co., Mineral Products Division
[4]Owens-Corning Fiberglass Corporation Compounding procedure: The polyester resin, low profile additive, zinc stearate and t-butyl perbenzoate were pre-blended in a one pint wide mouth jar by means of an air driven "Lightnin" mixer equipped with a Jiffy ® stirring blade consisting of a horizontal two bladed propeller with guard ring and two vertical blades. In the case of integral blend, the silane composition of Example 8 was added at this time. Complete wetting and dispersion of the zinc stearate was the major concern in the blending of these components.

The pre-blend was transferred to the mixing bowl of a Hobart N-50 mixer equipped with a dough hook. In the separate evaluations, untreated alumina trihydrate, pretreated alumina trihydrate and blend of DSC and untreated alumina trihydrate from Example 8 were added, in each case, in one charge (687.5 gm.) to the mixer bowl with the mixer stopped. The DSC and untreated alumina trihydrate which were not dry blended together were added to the liquid phase separately. The DSC was added first and mixed until it was completely wetted at which time the mixer was stopped and the untreated alumina trihydrate was added. Mixing continued until the running time of the mixer totaled six minutes. The mixer was run at speed 1 and six minutes was the standard mixing time for all fillers. During this period, the time for the filler to wet out and disperse in the liquid phase was recorded and set forth in Table 5 below.

TABLE 5

| | UNTREATED | INTEGRAL BLEND | ALL GHA-331 PRETREATED | DSC DRYBLENDED WITH GHA-331 | DSC & GHA-331 ADDED SEPARATELY | |
|---|---|---|---|---|---|---|
| Viscosity $10^3$ cps Brookfield RVT 10 RPM No. 6 Spindle 32° C. | 62.5 75 | 55 — | 42 — | 34.5 — | — 46 | |
| Time for Resin to Wet Filler (seconds) | 180 | 180 | 90 | 90 | 180 | After DSC dispersed, required 120 sec. to wet filler. |
| Dispersion of glass in filled resin | WORST | POOR | GOOD | GOOD | POOR | |

After the mixing of resin and filler, the sides of the bowl were scraped and the material collected in the center. A portion of the glass charge was spread around the sides of the bowl to stop the resin-filler mix from readhering. The mixer was turned on and run at speed 1 for 4 minutes. The remainder of the glass charge was added within the first 2 minutes of mixing. Composites were molded from the complete compound.

Test composites were prepared by placing 400 grams of bulk molding compound into single cavity, 8 × 8 × 0.125 inches, chrome plated mold. Mold surfaces were separated from the bulk molding compound by sheets of 0.003 inches thick MYLAR® film. Composites were pressed under 40 tons of force for 2 minutes at 300° F.

Composites were reduced to 6 × 6 inches by removing the outside inch of material from all sides. Ten 3 × 0.5 × 0.181 – 0.232 inches thick test specimens (depending on composite thickness) were cut from each composite.

Five test specimens were selected randomly for dry flexural testing. The remaining five specimens were immersed in boiling water for eight hours. Testing was done in accordance with ASTM 790-71. The results are set forth in Table 7 below.

TABLE 7

|  | UNTREATED | | INTEGRAL BLEND | | ALL ATH PRETREATED | | DLC DRYBLENDED WITH ATH | | DLC & ATH ADDED SEPARATELY | |
| --- | --- | --- | --- | --- | --- | --- | --- | --- | --- | --- |
|  | Dry | Wet | Dry | Wet | Dry | Wet | Dry | Wet | Dry | Wet |
| Flexural strength, psi: | 8300 | 8000 | 94000 | 6100 | 10700 | 7900 | 12300 | 11600 | 10500 | 7600 |
| Standard Error, % | 18.6 | 20.7 | 10.6 | 12.6 | 13.8 | 9.1 | 5.5 | 11.5 | 17.8 | 18.0 |
| Flexural Modulus, psi; | $2.15 \times 10^6$ | $1.90 \times 10^6$ | $2.24 \times 10^6$ | $1.7 \times 10^6$ | $2.23 \times 10^6$ | $1.79 \times 10^6$ | $2.25 \times 10^6$ | $1.79 \times 10^6$ | $2.21 \times 10^6$ | $1.67 \times 10^6$ |
| Standard Error, % | 8.75 | 5.35 | 5.9 | 8.0 | 5.8 | 5.5 | 4.5 | 4.0 | 4.8 | 4.9 |

What is claimed is:

1. A composition comprising alumina trihydrate particles containing on their surfaces a silane, its hydrolyzates or resulting condensate, which silane possesses at least two to about three hydrolyzable groups bonded to the silicon thereof and an organic group which contains a polyalkylene oxide group, said silane being present on the surfaces of said particles in an amount from about 0.25 weight percent to 5 weight percent of the composition.

2. The composition of claim 1 wherein the amount of the silane is from about 0.5 to about 3 weight percent of the composition.

3. The composition of claim 1 wherein the silane has the following general formula:

$$R^{II}(OR^I)_a ORSiX_3$$

wherein R can be any divalent organic group which is either oxygen or carbon bonded to the silicon atom, $R^I$ is one or more 1,2-alkylene groups each containing at least 2 carbon atoms and not more than about 4 carbon atoms; $R^{II}$ is hydrogen, alkyl, acyloxy or an organofunctional group; and X is a hydrolyzable group, and $a$ is a number having an average value of from 4 to about 150.

4. The composition of claim 3 wherein the silane is coreacted or comixed with a different silane, as encompassed by the following formula:

$$R^3_n(SiX_{4-n})_b$$

or the cohydrolyzate or the cocondensate of such different silane with the silane, wherein $R^3$ is an organic radical whose free valence is equal to the value of $b$, X is as defined above, $n$ is equal to 0 or 1 and $b$ is a positive number.

5. The composition of claim 3 wherein $a$ has a value of from 4 to about 120.

6. The composition of claim 4 wherein $a$ has a value of from 4 to about 120.

* * * * *

UNITED STATES PATENT OFFICE
CERTIFICATE OF CORRECTION

Patent No. 4,105,465         Dated August 8, 1978

Inventor(s) Sidney Ethan Berger

It is certified that error appears in the above-identified patent and that said Letters Patent are hereby corrected as shown below:

In the table of formulas appearing on columns 6 and 7, the seventh formula should read:

In column 19, in the table accompanying Example 7, the correct Flexural Strength value for Silicone D should read -- 9900-- not "9990".

Signed and Sealed this

Sixth Day of February 1979

[SEAL]

Attest:

RUTH C. MASON
Attesting Officer

DONALD W. BANNER
Commissioner of Patents and Trademarks